United States Patent [19]

Brandt et al.

[11] 4,180,438
[45] Dec. 25, 1979

[54] PROCESS FOR THE PREPARATION OF SUMP PRODUCT

[75] Inventors: Hans-Walter Brandt, Odenthal; Ludwig Deibele, Cologne; Kurt Toepffer; Karl-Heinz Steinacker, both of Leverkusen, all of Fed. Rep. of Germany

[73] Assignee: Bayer Aktiengesellschaft, Leverkusen, Fed. Rep. of Germany

[21] Appl. No.: 724,052

[22] Filed: Sep. 16, 1976

Related U.S. Application Data

[63] Continuation of Ser. No. 596,706, Jul. 17, 1975, abandoned.

[30] Foreign Application Priority Data

Aug. 9, 1974 [DE] Fed. Rep. of Germany ....... 2438290

[51] Int. Cl.² .............................................. B01D 1/22
[52] U.S. Cl. .................................. 203/89; 159/11 R; 159/49; 260/563 C; 544/106; 203/DIG. 25
[58] Field of Search .................... 423/659 R, 499, 204; 544/106; 260/563 C; 203/89, 95, 96; 202/234, 236; 159/4 R, 4 E, 4 D, 4 F, 6 R, 6 W, 11 R, 8, 13 C, 16 S, 13 A, 5, 49

[56] References Cited

U.S. PATENT DOCUMENTS

| 2,215,189 | 9/1940 | Peterson ...................... 203/89 |
| 2,964,513 | 12/1960 | Dale ........................... 159/16 S |
| 3,296,240 | 1/1967 | MacDonald ................ 159/13 C |
| 3,336,967 | 8/1967 | Ward .......................... 159/16 S |
| 3,421,567 | 1/1969 | Hoppe ........................ 159/16 S |
| 3,436,319 | 4/1969 | Von Horst et al. ............ 203/89 |
| 3,476,656 | 11/1969 | Van Tassel et al. ........... 203/89 |
| 3,737,378 | 6/1973 | Mori et al. ................. 159/16 S |
| 3,956,060 | 5/1976 | Scoggin ...................... 159/16 S |

OTHER PUBLICATIONS

R. H. Perry's "Chem. Engineers' Handbook", 4th Ed., (1963), Chapter 13, pp. 20 and 21, MacGraw-Hill Book Co., N. Y.

Primary Examiner—Wilbur L. Bascomb, Jr.
Attorney, Agent, or Firm—Sprung, Felfe, Horn, Lynch & Kramer

[57] ABSTRACT

A thin layer evaporator which has a vapor lock above the solvent inlet is used for the preparation of distillate-free sump product which is obtained as solid from the concentration of solutions of water, organic substances and non-volatile constituents and dissolved in solvents.

7 Claims, 1 Drawing Figure

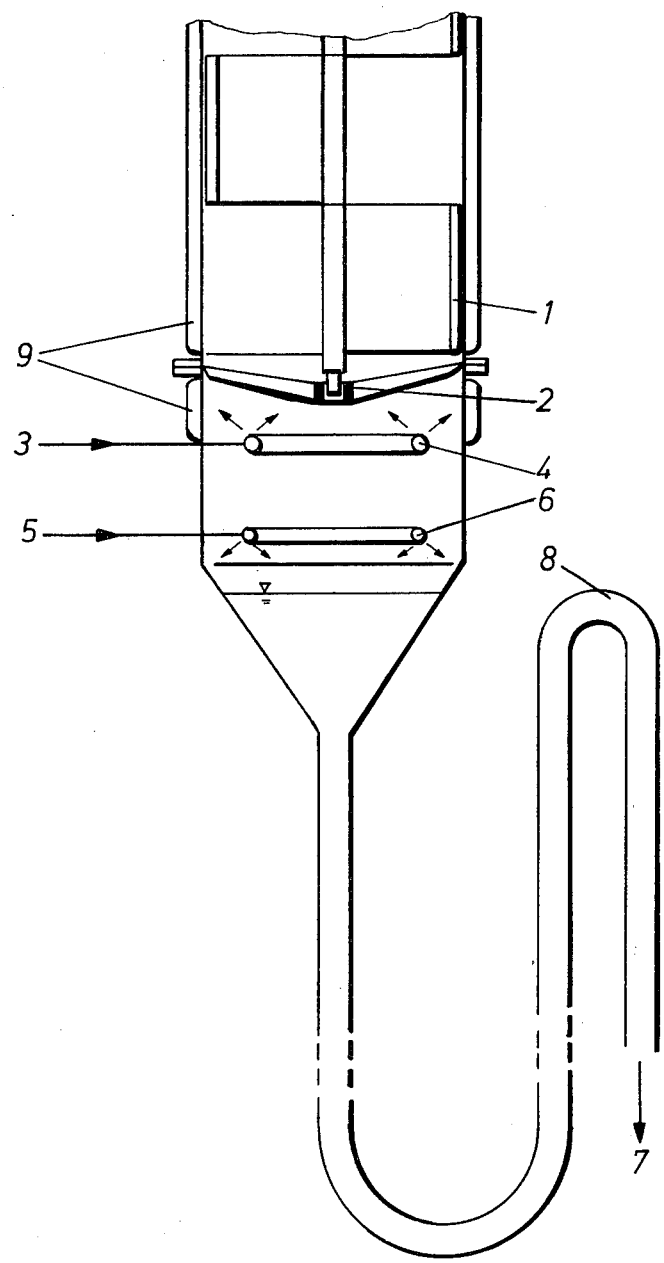

PROCESS FOR THE PREPARATION OF SUMP PRODUCT

This is a continuation of application Ser. No. 596,706, filed July 17, 1975 now abandoned.

This invention relates to a process for the preparation of a distillate-free sump product in thin layer evaporators, which sump product is obtained by the concentration of solutions comprising water, organic substances and non-volatile constituents to form a solid which is then dissolved in a solvent.

In thin layer evaporators it is frequently necessary to solve the problem of concentrating solutions of water, organic substances and non-volatile constituents. If the organic substances have a higher boiling point than water or if they form an azeotropic mixture with water, then the water must be evaporated together with the organic substance in order that the organic substance may be recovered. The water is then removed from the organic substance in a subsequent operation. The non-volatile constituents are obtained as solids in the lower part of the thin layer evaporator.

These solids can be removed semicontinuously from the thin layer evaporator by means of alternate receivers or continuously by means of rotary air lock extractor or screw conveyors. If the solids are removed continuously, the apparatus used for removing them can only be effectively sealed off from the thin layer evaporator with great difficulty. To ensure complete removal of the solid material from the sump of the thin layer evaporator, it is therefore often dissolved in a suitable solvent before it is continuously removed by known methods. Since the solvent used for this purpose is at a lower temperature then the walls of the thin layer evaporator, vapours of distillate which are normally removed at the head of the apparatus condense in the solvent. Consequently, the sump product of a thin layer evaporator cannot be obtained in a pure form and always contains some distillate. This not only reduces the efficiency of thin layer evaporators but also in many cases necessitates considerable effort to purify the sump products.

It is an object of this invention to provide a process by which sump products dissolved in solvent can be obtained completely free from distillate in thin layer evaporators.

According to the invention, this problem is solved by providing a vapour lock above the solvent inlet.

The particular advantages achieved by the process according to the invention lie in the fact that the vapour lock, which is produced by injecting a gas, produces a stream against the direction of the solids descending through the apparatus, so that the vapours of distillate are prevented from descending as far as the solvent and condensing there. The gas used for producing the vapour lock, which must not enter into any undesirable reactions with the distillate, is removed at the head of the thin layer evaporator together with the distillate and subsequently separated.

According to a further embodiment of the process of the invention, steam is used to form the vapour lock.

The particular advantages thereby achieved lie in the fact that no foreign substance is introduced into the distillate of the thin layer evaporator. Since, in the problem which is required to be solved here, water must in any case be evaporated together with the organic substance, no additional problem arises in the subsequent course of the process when steam is used as the vapour lock.

A practical example of the process according to the invention is illustrated in the drawing and described below.

The FIGURE is a schematic representation of a thin layer evaporator having a vapour lock.

The non-volatile constituents of the solution accumulate as solid below the bottom wiper blade 1 of the thin layer evaporator. The vapour lock is situated just below a bearing 2 of the shaft for the wiper blades. Steam is introduced into a spray ring 4 from a pipe 3. The spray ring directs the steam obliquely upwards. About 10 to 100 cm below the spray ring 4 is a second spray ring 6 through which the solvent required for dissolving the solid is introduced into the lower part of the thin layer evaporator from a pipe 5. The dissolved solid is continuously removed through a pipe 7 by way of a siphon 8. Heating jackets 9 which extend down the evaporator as far as the vapour lock keeps the thin layer evaporator at a sufficiently high temperature to prevent the condensation of distillate vapour.

Two examples of processes according to the invention are described below.

EXAMPLE 1

A solution of 70% of morpholine, 12% of water and 18% of sodium chloride is evaporated at normal pressure in a thin layer evaporator. The boiling point of morpholine at normal pressure is 128° C. The distillate from the thin layer evaporator is a mixture of morpholine and water, and the sump product is sodium chloride in the form of a powder. The solvent used to dissolve the sodium chloride is water.

When the solution was introduced at the rate of 1000 kg/hour the quantity of steam required for the vapour lock was 100 kg/hour and the quantity of solvent required so as to recover a 20% sodium chloride solution was 720 kg of water per hour. The water is introduced at a temperature of 80° C. so that condensation of the steam used as vapour lock is prevented as far as possible. No distillate could be detected in the dissolved sump product in a test carried out with a lower limit of detectability of 0.1%.

EXAMPLE 2

A solution of 25% of water, 55% of cyclohexylamine and 20% of organic residues is evaporated in a thin layer evaporator at normal pressure. Cyclohexylamine and water form a homogeneous azeotropic mixture at 96.4° C. and 55.8% water at normal pressure. The distillate from the thin layer evaporator is a mixture of cyclohexylamine and water while the non-volatile constituents accumulate as a granulate in the sump. The solvent used to dissolve the granulate is o-dichlorobenzene.

When 1000 kg/hour of solution were used, the quantity of steam required for the vapour lock was 80 kg/hour and the quantity of solvent required for producing a 30% solution was 470 kg/hour of o-dichlorobenzene. No distillate could be detected in the sump product.

What we claim is:

1. In the distillation of a solution comprising an organic substance, and non-volatile material which is precipitated as solid in the distillation, in a thin layer evaporator, comprising the steps of distilling the solution in the thin layer evaporator to evaporate the organic substance as overhead distillate product of the distillation and precipitate the non-volatile material as solids, collecting the precipitated solids as sump products, and adding a solvent which is at a lower temperature than the walls of the evaporator to the sump to take up the precipitated solids and removing the solvent containing the solids from the sump, the improvement which comprises introducing the solvent from outside the evaporator directly into the sump and providing a vapor lock adjacent to and above the level of the introduction of the solvent by injecting a stream of inert vapor through a first spray ring obliquely and upwardly and opposite the direction of the solvent to prevent condensation of distillate vapors by the solvent.

2. The process according to claim 1, wherein the solvent is introduced by a second spray ring disposed below the first spray ring.

3. The process according to claim 2, wherein the solvent is removed by siphoning same off by a siphon disposed below the second spray ring.

4. The process according to claim 3, further comprising heating the evaporator to a sufficiently high temperature to present condensation of the distillate vapor by providing a heating jacket extending down the evaporator to the vapor lock.

5. Process of claim 1, wherein the organic substance is morpholine, the non-volatile material is sodium chloride, and the solvent is water.

6. Process of claim 1, wherein organic substance is cyclohexylamine, the non-volatile material is organic residue and the solvent is o-dichlorobenzene.

7. The process according to claim 1, wherein the solvent is sprayed into the evaporator obliquely and downwardly through a second spray ring disposed below the first spray ring.

* * * * *

UNITED STATES PATENT AND TRADEMARK OFFICE
CERTIFICATE OF CORRECTION

PATENT NO. : 4,180,438
DATED : December 25, 1979
INVENTOR(S) : Hans-Walter Brandt, et al It is certified that error appears in the above-identified patent and that said Letters Patent are hereby corrected as shown below:

Col. 4, line 6, "present" should be --prevent--.

Signed and Sealed this

Twenty-fifth Day of March 1980

[SEAL]

Attest:

SIDNEY A. DIAMOND

Attesting Officer

Commissioner of Patents and Trademarks